(12) United States Patent
Cornell et al.

(10) Patent No.: US 6,756,013 B1
(45) Date of Patent: Jun. 29, 2004

(54) COMPOSITIONS OF IODONIUM COMPOUNDS AND METHODS AND USES THEREOF

(75) Inventors: Stephen W. Cornell, Naperville, IL (US); David D. Cornell, Kingsport, TN (US); Paul W. Cornell, Oceanside, CA (US)

(73) Assignee: Cornell Development Corporation, LLC, Naperville, IL (US)

( * ) Notice: Subject to any disclaimer, the term of this patent is extended or adjusted under 35 U.S.C. 154(b) by 675 days.

(21) Appl. No.: 09/638,823

(22) Filed: Aug. 14, 2000

(51) Int. Cl.$^7$ ................................................ A61L 2/00
(52) U.S. Cl. ................................ 422/28; 71/88; 71/94; 422/32; 422/37; 549/294; 549/274; 549/313
(58) Field of Search .................... 422/28, 37, 32; 549/294, 285, 274, 313; 71/88, 94

(56) References Cited

U.S. PATENT DOCUMENTS

| | | | |
|---|---|---|---|
| 2,878,293 A | 3/1959 | Kinzer ........................ 260/607 |
| 3,207,660 A | 9/1965 | Cannon ........................ 167/30 |
| 3,264,355 A | 8/1966 | Cannon ..................... 260/606.5 |
| 3,422,152 A | 1/1969 | Doub .......................... 260/612 |
| 3,622,586 A | 11/1971 | Jezic .......................... 260/295 |
| 3,712,920 A | 1/1973 | Jezic ......................... 260/332.5 |
| 3,734,928 A | 5/1973 | Jezic ......................... 260/332.2 |
| 3,759,989 A | 9/1973 | Jezic .......................... 260/539 |
| 3,885,036 A | 5/1975 | Moyle ......................... 424/275 |
| 3,896,140 A | 7/1975 | Piepys et al. ................ 260/307 |
| 3,944,498 A | 3/1976 | Moyle ......................... 252/106 |
| 4,007,227 A | 2/1977 | Baker et al. ................. 260/566 |
| 4,071,514 A | 1/1978 | Ribbecke et al. ......... 260/22 M |
| 4,207,310 A | 6/1980 | Langford ..................... 424/150 |
| 4,483,984 A | 11/1984 | Flagg ........................... 544/85 |
| 4,500,339 A | * | 2/1985 | Young et al. ................ 504/151 |
| 4,513,137 A | 4/1985 | Koser et al. .................. 546/14 |
| 4,613,620 A | 9/1986 | Cannon ........................ 514/570 |
| 4,648,988 A | * | 3/1987 | Van Dijck et al. .......... 252/602 |
| 5,106,407 A | 4/1992 | Relenyi et al. ................ 71/88 |
| 5,277,767 A | 1/1994 | Cushman et al. ............. 204/59 |
| 5,531,893 A | 7/1996 | Hu et al. ................ 210/500.35 |
| 5,631,277 A | 5/1997 | Romer et al. ................ 514/441 |
| 5,753,183 A | 5/1998 | Ohr et al. ...................... 422/37 |
| 6,083,408 A | 7/2000 | Breitenback et al. ........ 210/753 |

FOREIGN PATENT DOCUMENTS

| | | |
|---|---|---|
| GB | 1 516 351 | 7/1978 |
| SU | 598921 | 3/1978 |

OTHER PUBLICATIONS

International Search Report for International Application No. PCT/US01/23213 filed Jul. 23, 2001.

"Effect of Tetracycline Antibiotics on Pierces Disease of Grapevine in Florida USA," D.L. Hopkins, Proceedings of the Florida State Horticultural Society, No. 92, 1979, pp. 284–285.

"Xylella Fastidiosa are Biofilm–Forming Phytopathogenic Bacteria," L.L.R. Marques et al., Phytopathology, vol. 91, No. 6 Supplement, Jun. 2001 , p S58.

* cited by examiner

Primary Examiner—Krisanne Thornton
(74) Attorney, Agent, or Firm—Wallenstein Wagner & Rockey, Ltd.

(57) ABSTRACT

The present invention provides a composition having biological activity. The composition includes from about 10 ppm to about 5000 parts iodonium salt. The composition also includes from about 100 ppm to about 300,000 ppm of a compound to act as a carrier of the iodonium compound. The carrier is selected from at least one of polyvinyl alcohols, polyvinyl acetates, polyethylene glycols, ethylene glycol and propylene glycol block copolymers, cellulosic polymers, polyesters, alkyd polymers. The composition also includes from about 50 ppm to about 50,000 ppm of a compound to render the composition compatible with a surface being treated. This component is selected from at least one of di-acids, acid anhydrides, polyfunctional acids, di-ethylene glycol, resorcinol and the like. The composition also includes an appropriate vehicle selected from at least one of water, acidified water, paint, primer, and petroleum distillates. The invention also includes numerous methods of using the above composition by applying the composition to a surface to be treated.

28 Claims, No Drawings

COMPOSITIONS OF IODONIUM COMPOUNDS AND METHODS AND USES THEREOF

TECHNICAL FIELD

The present invention provides compositions of iodonium salts and methods for using these compositions for air and water sterilization, nematode and fungi control, to minimize mollusk attachment to submerged surfaces, to control termites and other destructive insects and to minimize the effects of Pierce Disease and other such diseases transmitted through plant xylem.

BACKGROUND OF THE INVENTION

It is known in the art that a class of compounds comprising the hypervalent salts of iodine, known as iodonium compounds, is effective in killing bacterial, fungal, and viral pathogens. U.S. Pat. No. 3,422,152 discloses using dihalogenated alkoxydiphenyl iodonium salts as pharmaceutical anhelminitics. U.S. Pat. No. 3,885,036 discloses that certain diaryl iodonium salts can be biologically active yet exhibit low vertebrate toxicity and toxicity to aquatic environments. A new electrochemical method for synthesizing diaryl iodonium compounds has been developed and patented by Cushman, et. al. (U.S. Pat. No. 5,277,767), which is less costly and able to compete effectively with the traditional methods.

SUMMARY OF THE INVENTION

The present invention provides a composition having biological activity comprising: (1) from about 10 ppm to about 5000 parts iodonium salt, (2) from about 100 ppm to about 300,000 ppm of a compound to act as a carrier of the iodonium compound and is selected from the group consisting of polyvinyl alcohol, polyvinyl acetate, polyethylene glycol, ethylene glycol and propylene glycol block copolymers (poloxymers), cellulosic polymer, polyester, alkyd polymers and mixtures of the same; (3) from about 50 ppm to about 50,000 ppm of a compound to render the composition compatible with a surface being treated and is selected from the group consisting of di-acids, acid anhydrides, polyfunctional acids, di-ethylene glycol, resorcinol and the like; and (4) an appropriate vehicle selected from the group consisting of water, acidified water, paint, primer, and petroleum distillates.

The present invention further provides numerous methods of using the above compound by applying the compound to a surface to be treated.

DETAILED DESCRIPTION

While this invention is susceptible of embodiments in many different forms, and will herein be described in detail, preferred embodiments of the invention are disclosed with the understanding that the present disclosure is to be considered as exemplifications of the principles of the invention and are not intended to limit the broad aspects of the invention to the embodiments illustrated.

This invention describes a composition utilizing iodonium compounds, however synthesized, in a novel way to provide an effective kill level for air-borne and water-borne pathogens by treating filtration medium used to remove these pathogens from the air or fluid. The invention also describes a method for sterilization of soil against nematodes, fungi, and like pests. The invention further provides a method to prevent or minimize mollusk attachment to submerged surfaces. The invention further provides a method for treating submerged surfaces against termites and the like. The invention also provides a method to treat cellolosic plant xylem against bacterial infection spread by insects to valuable crops and plants through the xylem of the plant.

Suitable iodonium compounds of the present invention include iodonium compounds having the general formula $RI^+R'X^-$ where I is an iodine atom, R and ' are the same or different organic groups. Suitable organic groups include aryl, aryloxy and heterocyclic groups.

Suitable aryl groups include aromatic compounds, single ring aromatic compounds, and polycyclic compounds. Suitable single ring aromatic compounds will have from 5–8 carbons. In a preferred form of the invention the preferred organic group is a 6 membered phenyl or benzyl ring. Suitable polycyclic compounds include both benzenoid aromatic compounds, those containing only benzene rings, and non-benzenoid compounds which contain aromatic rings other than six-membered benzene rings but may contain benzene rings. Suitable benzenoid aromatic compounds include those having from 2 to 10 benzene rings and more preferably from 2 to 4 benzene rings and include naphthalene, anthracene, phenathrene, pyrene, 1,2-benzopyrene, coronene and the like. Suitable non-benzenoid rings include two or more rings each having from 4 to 12 carbons and include, azulene, and bridged polycyclic compounds such as norbornene, norbornadiene and the like.

Suitable heterocyclic groups include single-ringed compounds or multiple-ringed compounds where at least one of the rings have dissimilar atoms in the ring. In a preferred form of the invention the heterocyclic group will have one or more rings with one ring being a carbon ringed compound having one or more non-carbon atoms interposed in the ring structure. Suitable non-carbon atoms include nitrogen, oxygen, sulfur and combinations of the same. The heterocyclic group can be saturated or unsaturated. Accordingly, suitable heterocyclic compounds include, but are not limited to, pyrrole, pyrazole, imidazole, indole, pyridine, pyridazine, pyrimidine, quinoline, piperidine, pyrrolidine, thiazole, purine, thiophene, benzothiophene and furan, to name a few. In a preferred form of the invention the heterocyclic compound is either a thiazole, thiophene or benzothiophene.

It is also possible that the organic groups set forth above can be substituted with groups such as halides, alkyl groups, alkoxy, vinyl groups, carboxylic acids, esters of carboxylic acids, ethers, alcohols, and epoxides and the like. Suitable alkyl groups have from 1 to 18 carbons and can be straight chain, cyclic or polycylic in structure. Suitable alkoxy groups include those having from 1 to 18 carbon atoms to define a backbone with one or more oxygen atoms interposed therein. In a preferred form of the invention the organic compound is a substituted phenyl, namely toluol. In a preferred form of the invention the ester is a cyclic ester and more preferably maleic anhydride. In general, the optional substituents can be any group or groups that do not have substantial adverse effects on preparation of the desired diaryliodonium compound.

The iodonium compounds of the present invention are, in a preferred form of the invention, prepared using the process set forth in U.S. Pat. No. 5,277,767 which has been incorporated herein and made a part hereof in its entirety.

II. Composition for Delivering the Iodonium Compounds

The iodonium compounds set forth above can be incorporated into an appropriate vehicle for such diverse applications and uses as water and air sterilization, nematode and fungi control, deterring mollusk attachment to submerged surfaces, deterring termite infestation, eradicating or minimizing Pierce Disease and other similar plant diseases, and controlling mildew and treating flooded homes. In general, these applications shall be referred to as treatment of surfaces.

The vehicle preferably is a composition having one or more of the iodonium compounds set forth above, which shall sometimes be referred to as the active compound, with additional components to assist in carrying or delivering (the carrier) the active compound by the selected or most efficacious application technique, additional components to assist in compatibilizing the active compound and the carrier with the surface to be treated.

A suitable composition includes: (1) from about 10 ppm to about 5000 ppm, more preferably from about 25 ppm to about 1000 ppm even more preferably from about 50 ppm to about 500 ppm and most preferably from about 50 ppm to about 150 ppm of one or more of the iodonium compounds set forth above, (2) from about 100 ppm to about 300,000 ppm, more preferably from about 500 ppm to about 50,000 ppm, even more preferably from about 1000 ppm to about 20,000 ppm and most preferably from about 1000 ppm to about 2000 ppm of a carrier selected from the group of polyvinyl alcohol, polyvinyl acetate, polyethylene glycol, ethylene glycol and propylene glycol block copolymers (poloxymers), cellulosic polymer, polyester, alkyd polymer and mixtures of the same; (3) from about 50 ppm to about 1000 ppm, more preferably from about 100 ppm to about 500 ppm and even more preferably from about 100 ppm to about 300 ppm of a compound to render the composition compatible with a surface being treated and is selected from the group consisting of di-acids, acid anhydrides, polyfunctional acids, di-ethlene glycol, resorcinol and the like; and (4) an appropriate vehicle selected from the group consisting of water, acidified water, paint, primer, and petroleum distillates.

Optionally, other adjuvants known by those skilled in the art may be added to the composition such as stabilizers, surfactants, initiators, flow control agents and leveling agents and the like.

The composition is prepared by blending the above components in a suitable mixing mechanism. Suitable mixing mechanisms include any of the class of mixing equipment for tumbling, stirring, beating, folding, quartering and the like of the components of the composition. The composition can be prepared as a full strength liquid, or as a masterbatch or concentrate, such that when let down will produce the composition of this invention. In certain instances it is desirable as a practice of this invention to make the initial composition either more or less concentrated, since the environment will adjust the liquid of the composition to provide the desired concentration.

III. Methods for Using the Compositions

The compositions of the present invention can be used for treating a variety of surfaces. To remove air-borne and water-borne contaminants the compositions of the present invention can be applied to a filter media, such as the cellulosic type filter media that are well known in the art. The compositions are applied to the filter medium by any of the means known to those skilled in the art. Such means include, but are not restricted to, spraying, dipping, brushing, roller painting, or coating. Once the solution is applied to the filtration medium, the medium is dried, baked, or otherwise dewatered by any of the means known to those skilled in the art to drive the reaction of the moieties to produce an interpenetrating network (IPN) of the esterified adducts with the medium fibers. The IPN will hold the iodonium compound on the surface of the filtration medium, such that the area for it to interact with the pathogens is sufficient to filter them out, and the concentration of iodonium is sufficient to kill them. The IPN is permanent and cannot be washed out by the application of fresh water to the filter, either as nascent liquid, or as vapor present in the air.

As another feature of this invention, the filtration medium so treated with the iodonium adduct IPN can be irradiated with light of the proper wavelength to cause the iodonium salt to be photolized and become a chromophore. Said chromophore permits the visual observation of the extent of coverage of the filtration medium with the solution/compound. In most instances it will be desirable to leave the iodonium salt in this photolized state, since data has shown that the iodonium in this state is biologically active. Also, certain of the iodonium compounds set forth above, and in particular where R and R' are phenyl groups, the composition is fluorescent to varying wavelengths of ultraviolet light and scanning with "black light" can show deposition of the iodonium-containing mixture.

However, in some instances, after proving the location of the iodonium and its concentration, it is desirable to not have the yellow color present, the reverse reaction, known by those skilled in the art to quench the radicals which promote the chromophore, can be applied to decolorize the filtration medium. Radical quencher stabilizers known to those skilled in the art are useful in this regard.

The present invention further provides a method for delivery of the above-described compositions for sterilization of soil against fungi, nematodes, and other pests. The compositions are applied to the infected or potentially infected soil by any of the means known to those skilled in the art including, but not restricted to, spraying, drip irrigation, rototilling, or other means of incorporating the composition into the soil. The preferred means of application is by drip irrigation tubing having an outlet positioned under agricultural mulch film. Once the solution is applied to the soil, the sunlight heats the ground to drive the moisture away and produce the lethal dosage to kill the fungi, nematodes, bacteria, and like pests. The polyethylene glycol or polyvinyl alcohol moieties are preferably included and are believed to provide a substrate to hold the iodonium compound; helping disperse the iodonium compound through the drip irrigation tubing; acting as a soil conditioner; and creating a concentration of iodonium sufficient to kill the nematodes, fungi, and other pests.

One further specific use for the present invention is for the treatment of tissue such as animal or plant tissue. One preferred use is for the treatment of plants tissue is in the viniculture industry for combating Pierce Disease. Pierce Disease is caused by the bacteria Xylella fastidiosa. The preferred administration method is by drip irrigation of the solution to the soil around the vines. During the transport of water from the root system to the rest of the plant, the xylem of the vine retains the iodonium compound, which is specifically formulated to interact with the xylem. In this way the iodonium compound becomes a systemic poison to the Xylella fastidiosa. Introduction of the iodonium into the drip irrigation system proves to be the most effective means; however, other means known to those skilled in the art of viniculture for the watering of vines and fruit trees can also effectively be used, since the composition is specifically tailored in the concentration of its components to deliver the iodonium compound most effectively to the xylem of the plant. The formulation prevents an adverse partitioning of iodonium within the plant so as to minimize the amount of iodine in the grape, which might impart an off taste to the wine.

Yet another aspect of the present invention provides a composition to deter mollusk attachment to submerged surfaces such as surfaces submerged under water.

Yet another aspect of the present invention provides a composition to treat submerged wood surfaces to control termites. The composition of the present invention is applied to wood. When termites eat the treated wood the active compound kills the bacteria in the gut of the termite responsible for digesting the consumed wood. Eventually the termite dies of starvation. The soil surrounding the submerged wood can also be treated with the composition and can be effective in controlling termites.

For anti-mildew applications the iodonium salt of the present invention is incorporated into household sprays for topical applications to sanitary surfaces.

Yet another aspect of the present invention provides a composition to be used to for treating areas in a home after flooding to kill water-borne pathogens and to prevent or diminish mildew and mold damage to structures. The composition can be incorporated into shampoos and other cleaning compounds for cleaning carpeting, wall and ceiling surfaces and other living and working space surfaces.

While specific embodiments have been illustrated and described, numerous modifications come to mind without significantly departing from the spirit of the invention, and the scope protection is only limited by the scope of the accompanying claims. For example, the present invention can be varied to provide bonding between dissimilar but compatible substrate materials.

We claim:

1. A composition having biological activity comprising:
   from about 10 ppm to about 5000 ppm iodonium salt;
   from about 100 ppm to about 300,000 ppm of a compound selected from the group consisting of polyvinyl alcohols, polyvinyl acetates, polyethylene glycols, ethylene glycol and propylene glycol block copolymers, cellulosic polymers, polyesters, and alkyd polymers;
   from about 50 ppm to about 50,000 ppm of a compound to render the composition compatible with a surface being treated, the compound selected from the group consisting of di-acids, acid anhydrides, polyfunctional acids, di-ethylene glycol, and resorcinol;
   an appropriate vehicle selected from the group consisting of water, acidified water, paint, primer, and petroleum distillates.

2. The composition of claim 1 wherein the iodonium salt have the formula $RI^+R'X^-$ where I is an iodine atom, R and R' are the same or different organic groups.

3. The composition of claim 2 wherein the organic group is selected from the group consisting of: aryl, aryloxy and heterocyclic groups.

4. The composition of claim 3 wherein the aryl groups are selected from the compounds consisting of aromatic compounds, single ring aromatic compounds, and polycyclic compounds.

5. The composition of claim 4 wherein the single ring aromatic compounds will have from 5 to 8 carbons.

6. The composition of claim 4 wherein the polycyclic compounds are selected from the group consisting of benzenoid aromatic compounds, and non-benzenoid compounds.

7. The composition of claim 6 wherein the benzenoid aromatic compounds have from 2 to 10 benzene rings.

8. The composition of claim 7 wherein the benzenoid aromatic compound is selected from the group consisting of naphthalene, anthracene, phenathrene, pyrene, 1,2-benzopyrene, and coronene.

9. The composition of claim 6 wherein the non-benzenoid rings include two or more rings each ring having from 4 to 12 carbons.

10. The composition of claim 3 wherein the heterocyclic groups are single-ringed compounds or multiple-ringed compounds where at least one of the rings have dissimilar atoms in the ring.

11. The composition of claim 10 wherein the heterocyclic ring has carbon atoms and at least one non-carbon atom selected from the group consisting of nitrogen, oxygen, and sulfur.

12. The composition of claim 10 wherein the heterocyclic ring can be saturated or unsaturated.

13. The composition of claim 10 wherein the heterocyclic ring is selected from the group consisting of pyrrole, pyrazole, imidazole, indole, pyridine, pyridazine, pyrimidine, quinoline, piperidine, pyrrolidine, thiazole, purine, thiophene, benzothiophene and furan.

14. The composition of claim 3 wherein the organic compound can be substituted with groups selected from the group consisting of halides, alkyl groups, alkoxy groups, vinyl groups, carboxylic acids, esters, ethers, alcohols, and epoxides.

15. The composition of claim 14 wherein the alkyl groups have from 1 to 18 carbons.

16. The composition of claim 14 wherein the alkyl group is selected from straight chain, cyclic or polycyclic alkyls.

17. The composition of claim 14 wherein the alkoxy group have from 1 to 18 carbons to define a backbone and have at least one oxygen atom in the backbone.

18. The composition of claim 1 wherein the composition is a paint for application of a surface submerged below water or soil.

19. The composition of claim 1 wherein the composition is applied to a filter media.

20. A method for using an iodonium composition comprising the steps of:
    providing a composition comprising from about 10 ppm to about 5000 ppm iodonium salt, from about 100 ppm to about 300,000 ppm of a compound selected from the group consisting of polyvinyl alcohols, polyvinyl acetates, polyethylene glycols, ethylene glycol and propylene glycol block copolymers, cellulosic polymers, polyesters, and alkyd polymers; from about 50 ppm to about 50,000 ppm of a compound to render the composition compatible with a surface being treated, the compound selected from the group consisting of di-acids, acid anhydrides, polyfunctional acids, di-ethylene glycol and resorcinol; and an appropriate vehicle selected from the group consisting of water, acidified water, paint, primer, and petroleum distillates; and
    applying the composition to a surface to be treated.

21. The method of claim 20 wherein the step of applying the composition to a surface includes the techniques of: spraying, dipping, brushing, roller painting, coating, drip irrigation, and rototilling.

22. The method of claim 20 wherein the surface is a filter media.

23. The method of claim 22 wherein the step of applying the composition to the surface further includes the step of:
    dewatering the filter media.

24. The method of claim 23 wherein the dewatering step includes the step of creating an interpenetrating network to adhere the composition to the surface.

25. The method of claim 23 further comprising the step of irradiating the filter to cause the iodonium salt to be photolized.

26. The method of claim 20 wherein the surface is soil.

27. The method of claim 20 wherein the surface is wood.

28. The method of claim 20 wherein the surface is a xylem of a plant.

* * * * *

UNITED STATES PATENT AND TRADEMARK OFFICE
CERTIFICATE OF CORRECTION

PATENT NO.     : 6,756,013 B1
DATED          : June 29, 2004
INVENTOR(S)    : Stephen W. Cornell, David D. Cornell and Paul W. Cornell It is certified that error appears in the above-identified patent and that said Letters Patent is hereby corrected as shown below:

<u>Column 2,</u>
Line 10, please delete "R and ' are the same" and insert -- R and R' are the same -- therefor.

Signed and Sealed this

Twenty-seventh Day of September, 2005

JON W. DUDAS
*Director of the United States Patent and Trademark Office*